(12) United States Patent
Suzuki et al.

(10) Patent No.: US 10,073,280 B2
(45) Date of Patent: Sep. 11, 2018

(54) METHOD FOR ASSESSING SPECTACLE LENS BY EVOKED ACTIVITY IN VISUAL CORTEX OF BRAIN OR THE LIKE, AND METHOD FOR DESIGNING SPECTACLE LENS USING SAID METHOD FOR ASSESSMENT

(71) Applicants: Tokai Optical Co., Ltd., Okazaki-shi, Aichi (JP); Inter-University Research Institute Corporation National Institutes of Natural Sciences, Okazaki-shi, Aichi (JP)

(72) Inventors: Masaya Suzuki, Okazaki (JP); Yuko Nagata, Okazaki (JP); Koji Inui, Okazaki (JP); Yasuyuki Takeshima, Okazaki (JP); Ryusuke Kakigi, Okazaki (JP)

(73) Assignees: TOKAI OPTICAL CO., LTD., Okazaki-Shi, Aichi (JP); INTER-UNIVERSITY RESEARCH INSTITUTE CORPORATION NATIONAL INSTITUTES OF NATURAL SCIENCES, Okazaki-Shi, Aichi (JP)

( * ) Notice: Subject to any disclaimer, the term of this patent is extended or adjusted under 35 U.S.C. 154(b) by 834 days.

(21) Appl. No.: 14/403,864

(22) PCT Filed: Oct. 9, 2012

(86) PCT No.: PCT/JP2012/076075
§ 371 (c)(1),
(2) Date: Nov. 25, 2014

(87) PCT Pub. No.: WO2013/179507
PCT Pub. Date: Dec. 5, 2013

(65) Prior Publication Data
US 2015/0133811 A1 May 14, 2015

(30) Foreign Application Priority Data
May 30, 2012 (JP) ................................. 2012-122917

(51) Int. Cl.
*A61B 5/0484* (2006.01)
*A61B 5/04* (2006.01)
(Continued)

(52) U.S. Cl.
CPC ................ *G02C 7/027* (2013.01); *A61B 3/10* (2013.01); *A61B 5/04012* (2013.01); *A61B 5/04842* (2013.01); *G02C 7/025* (2013.01)

(58) Field of Classification Search
CPC .......... G02C 7/027; G02C 7/025; A61B 3/10; A61B 5/04012; A61B 5/04842
(Continued)

(56) References Cited

U.S. PATENT DOCUMENTS 3,574,450 A * 4/1971 White ...................... A61B 3/10
351/222
4,181,407 A * 1/1980 Razran ................... A61B 3/103
351/205
(Continued)

FOREIGN PATENT DOCUMENTS

EP 2856929 A1 * 4/2015 ............... A61B 3/10
JP 61-249433 11/1986
(Continued)

OTHER PUBLICATIONS

International Preliminary Report on Patentability for PCT/JP2012/076075, dated Dec. 2, 2014 (9 pages).
(Continued)

*Primary Examiner* — Navin Natnithithadha
(74) *Attorney, Agent, or Firm* — Bookoff McAndrews, PLLC

(57) ABSTRACT

[Problem] To provide an evaluation method for evaluating spectacle lenses that is capable of objectively evaluating
(Continued)

spectacle lenses suitable for a user by measuring brain activity, and a design method for designing spectacle lenses using the evaluation method.

[Solution] A subject is allowed to wear to-be-evaluated lenses, and the subject is allowed to visually observe a visual stimulus object used to evoke an activity of a specific part of the visual cortex of the brain through the to-be-evaluated lenses, and an evoked activity of the specific part of the brain's visual cortex when the visual stimulus object is visually observed by the to-be-evaluated lenses is measured by an electroencephalograph or by a magnetoencephalograph, and the spectacle lenses are evaluated based on time (latency) from when a visual stimulus is received till when a change is caused thereby or based on the magnitude (amplitude) of activity.

20 Claims, 13 Drawing Sheets

(51) Int. Cl.
  *G02C 7/02* (2006.01)
  *A61B 3/10* (2006.01)
(58) Field of Classification Search
  USPC .................................................. 600/544, 545
  See application file for complete search history.

(56) References Cited

U.S. PATENT DOCUMENTS

| | | | |
|---|---|---|---|
| 4,697,598 A | 10/1987 | Bernard et al. | |
| 4,709,702 A | 12/1987 | Sherwin | |
| 4,861,154 A * | 8/1989 | Sherwin | A61B 3/02 351/205 |
| 4,953,968 A * | 9/1990 | Sherwin | A61B 3/02 351/211 |
| 5,052,401 A * | 10/1991 | Sherwin | A61B 3/02 329/358 |
| 5,331,969 A * | 7/1994 | Silberstein | A61B 5/0478 600/544 |
| 7,740,592 B2 * | 6/2010 | Graham | A61B 5/04842 348/68 |
| 7,972,278 B2 * | 7/2011 | Graham | A61B 5/04842 600/544 |
| 9,230,062 B2 * | 1/2016 | Seriani | G06F 19/3418 |
| 2003/0158497 A1 * | 8/2003 | Graham | A61B 5/04842 600/558 |
| 2009/0076406 A1 * | 3/2009 | Graham | A61B 5/04842 600/544 |
| 2009/0153796 A1 * | 6/2009 | Rabner | A61B 3/0091 351/201 |
| 2011/0218456 A1 * | 9/2011 | Graham | A61B 5/04842 600/558 |
| 2014/0129259 A1 * | 5/2014 | Seriani | G06F 19/3418 705/3 |
| 2015/0133811 A1 * | 5/2015 | Suzuki | A61B 3/10 600/544 |
| 2016/0242670 A1 * | 8/2016 | Suzuki | G02C 7/027 |

FOREIGN PATENT DOCUMENTS

| | | | |
|---|---|---|---|
| JP | 61-249436 | 11/1986 | |
| JP | 64-040028 | 2/1989 | |
| JP | 09-238903 | 9/1997 | |
| JP | 10-097369 | 4/1998 | |
| JP | 11-076185 | 3/1999 | |
| JP | 2005-034620 | 2/2005 | |
| JP | WO 2013179507 A1 * | 12/2013 | ............... A61B 3/10 |

OTHER PUBLICATIONS

Iwasaki, W., "Morphological evaluation of visual sense with contact lens wear," *Folia Ophthalmogica Japonica*, vol. 39, No. 7, pp. 1222-1225 (1988).

Iwasaki, W. et al., "Study on Contact Lens Wear and Corneal Safety. The 10$^{th}$ Report: Visual Sense of Form During Contact Lens and IOL Use," *Journal of Japan Contact Lens Society*, vol. 31, No. 3, pp. 207-213 (1989).

* cited by examiner (a)　　　　　　　　(b)

Direction in which electric current flows
from activity source toward forward end Position (a)

(b)

(a)

(b)

METHOD FOR ASSESSING SPECTACLE LENS BY EVOKED ACTIVITY IN VISUAL CORTEX OF BRAIN OR THE LIKE, AND METHOD FOR DESIGNING SPECTACLE LENS USING SAID METHOD FOR ASSESSMENT

This application is a national stage filing under 35 U.S.C. § 371 of International Application No. PCT/JP2012/076075, filed on Oct. 9, 2012, incorporated by reference herein in its entirety, which claims the benefit of priority to Japanese Patent Application No. 2012-122917, filed on May 30, 2012.

TECHNICAL FIELD

The present invention relates to an evaluation method for evaluating spectacle lenses using the evoked activity of a visual cortex or the like of the brain and a design method for designing spectacle lenses using the evaluation method.

BACKGROUND ART

When a user newly has spectacles made at an optician's store, lens diopter power that has been completely corrected or lens diopter power that has been derived from refraction measurement performed by, for example, an autorefractometer is not always best for the user, and, finally, lens conditions are selected in consideration of user's or inspector's subjective point of view. This applies to, for example, the additional diopter power of a progressive power lens, progressive design characteristics other than the additional diopter power, selection of a lens type such as a spherical lens or an aspherical lens, or selection of a color of sunglasses. As thus described, the specifications of spectacle lenses actually determined are not unambiguously decided.

CITATION LIST

Patent Literature

Japanese Published Unexamined Patent Application No. H10-97369

SUMMARY OF INVENTION

Technical Problem

Spectacle lenses are basically produced based on predetermined design data corresponding to specifications determined by a user's subjective point of view as described above, and are originally selected from among a group of lenses suitable for the user, and therefore there has been a desire to evaluate whether the specifications of lenses selected by the user are suitable for this user. Alternatively, when a user cannot decide which of spectacle lenses provided as suitable lenses is good, there has been a desire to obtain a criterion for its judgment. Alternatively, as to prototypes when lenses are developed, there has been a desire to obtain a criterion for objective judgment on which one of the prototypes is suitable for this user.

By the way, the human brain performs brain activity in response to external stimuli. The brain activity is accompanied by the activity of neurons, and therefore it is possible to measure brain waves (electric current) as a change in voltage indirectly from the outside, or it is possible to measure brain waves as a change in magnetic field (magnetic flux density). It is known that the time-dependent waveform of a brain wave or of a magnetic field (magnetic flux density) to be measured is not the same, and varies in accordance with external stimuli. Some techniques using such measurement of brain activity have been proposed. For example, Patent Document 1 discloses a technique in which a plurality of light sources that differ in blinking timing and that provide different visual stimuli are prepared, and a function is allocated to each light source, and, when the function is performed, brain waves are detected while gazing at a corresponding light source, and, as a result, the function is performed. Likewise, the present invention uses a technique that measures such brain activity.

It is an object of the present invention to provide an evaluation method for evaluating spectacle lenses that is capable of objectively evaluating spectacle lenses suitable for a user by measuring brain activity and to provide a design method for designing spectacle lenses that uses the evaluation method.

Solution to Problem

To solve the problem, in an example 1, the gist resides in allowing a subject to wear lenses to be evaluated, allowing the subject to visually observe a visual stimulus object used to evoke an activity of a specific part of the brain's visual cortex through the lenses to be evaluated, measuring an evoked activity of the specific part of the brain's visual cortex when the visual stimulus object is visually observed by the lenses to be evaluated, and evaluating the evoked activity of the brain's visual cortex.

In an example 2, the gist resides in separating an evoked activity of a primary visual cortex or an evoked activity of a secondary visual cortex from the evoked activity of the brain's visual cortex, and evaluating the evoked activity of the primary visual cortex separated therefrom or the evoked activity of the secondary visual cortex separated therefrom, in addition to the arrangement of example 1.

In an example 3, the gist resides in the fact that the visual stimulus object is disposed in a visual lower half area, in addition to the arrangement of example 1 or example 2.

In an example 4, the gist resides in the fact that the visual stimulus object consists of a combination of line segments, in addition to the arrangement of any one of example 1 to example 3.

In an example 5, the gist resides in the fact that the visual stimulus object consists of at least two kinds of visual stimulus objects that are equal to each other in total length of the line segments of which each visual stimulus object is formed, and the at least two kinds of visual stimulus objects are alternately presented, in addition to the arrangement of any one of example 1 to example 4.

In an example 6, the gist resides in the fact that the visual stimulus object is presented at a peripheral part away from a fixation point to which attention of the subject is paid when the subject is allowed to visually observe the visual stimulus object, in addition to the arrangement of example 5.

In an example 7, the gist resides in the fact that, when the subject is allowed to visually observe the visual stimulus object, the visual stimulus object is not presented within a visual angle of 8 degrees from the fixation point to which attention of the subject is paid, excluding the fixation point, in addition to the arrangement of any one of example 1 to example 6.

In an example 8, the gist resides in the fact that, as a spectacle lens condition, when a spectacle lens is evaluated by the evoked activity of the brain's visual cortex, earliness is preferable to lateness in time from when the visual stimulus object to evoke an activity of the specific part of the brain's visual cortex is presented till when an evoked activity appears, in addition to the arrangement of any one of example 1 to example 7.

In an example 9, the gist resides in the fact that, as a spectacle lens condition, when the evoked activity of the brain's visual cortex or the like is evaluated, largeness is preferable to smallness in magnitude of an activity evoked by presenting the visual stimulus object to evoke an activity of the specific part of the brain's visual cortex, in addition to the arrangement of any one of example 1 to example 3.

In an example 10, the gist resides in the fact that the visual stimulus is a contrast, and the evoked activity of the brain's visual cortex evoked by this contrast is evaluated, in addition to example 1 or example 2.

In an example 11, the gist resides in the fact that the visual stimulus object consists of a combination of chromatic colors, in addition to example 10.

In an example 12, the gist resides in the fact that the visual stimulus object is disposed in a visual lower half area, in addition to example 10 or example 11.

In an example 13, the gist resides in the fact that the visual stimulus object consists of a combination of line segments, in addition to any one of example 10 to example 12.

In an example 14, the gist resides in the fact that the visual stimulus object consists of at least two kinds of visual stimulus objects that are equal to each other in total length of the line segments of which each visual stimulus object is formed, and the at least two kinds of visual stimulus objects are alternately presented, in addition to the arrangement of example 13.

In an example 15, the gist resides in the fact that, as a spectacle lens condition, when a spectacle lens is evaluated by the evoked activity of the brain's visual cortex, earliness is preferable to lateness in time from when the visual stimulus object to evoke an activity of the specific part of the brain's visual cortex is presented till when an evoked activity appears, in addition to any one of example 10 to example 14.

In an example 16, the gist resides in the fact that the evoked activity measures a visual evoked field, and an evaluation is made based on a value of the visual evoked field, in addition to any one of example 1 to example 15.

In an example 17, the gist resides in the fact that the evoked activity measures a visual evoked potential, and an evaluation is made based on a value of the visual evoked potential, in addition to any one of example 1 to example 15.

In an example 18, the gist resides in the method for evaluating spectacle lenses by an evoked activity of a brain's visual cortex according to example 15 characterized in that, when the visual evoked potential is used, an evoked potential of an N130 component that is opposite in peak extreme value to a P100 component immediately after the P100 component evoked by visually stimulating the primary visual cortex is used for an evaluation, in addition to any one of example 1 to example 17.

In an example 19, the gist resides in the fact that the spectacle lens to be evaluated is an aspherical lens in which a shape of a peripheral lens part is changed little by little, in addition to any one of example 1 to example 18.

In an example 20, the gist resides in the fact that the spectacle lens to be evaluated is a progressive power lens in which a lens shape is changed little by little, in addition to any one of example 1 to example 18.

In an example 21, the gist resides in the fact that the spectacle lens to be evaluated is a lens whose spectral transmittance is changed by optical absorption or optical reflection, etc., in addition to any one of example 1 to example 20.

In an example 22, the gist resides in a method for designing spectacle lenses by using the method for evaluating spectacle lenses by an evoked activity of a brain's visual cortex or the like according to any one of example 1 to example 20.

In the aforementioned arrangement, a subject is first allowed to wear lenses to be evaluated, and is then allowed to visually observe a visual stimulus object through the to-be-evaluated lenses, and the evoked activity of a specific part of a brain's visual cortex obtained as a result is measured, and the to-be-evaluated lenses are evaluated.

The evoked activity measured concerning a single to-be-evaluated lens may be evaluated, and a plurality of to-be-evaluated lenses that are different in lens characteristics may be prepared, and the evoked activity measured concerning these lenses may be evaluated. The evaluation does not necessarily make it possible to select a lens having a best result. Herein, strictly, the point is that pieces of information that objectivity enable lens selection can be obtained by the evaluation.

The visual stimulus is defined as a stimulus used to evoke the activity of the specific part of the brain's visual cortex. The reason is that the evoked activity of the specific part of the brain's visual cortex or the like can be efficiently measured by setting the visual stimulus object as a visual stimulus object to evoke the activity of the specific part of the brain's visual cortex or the like that is targeted for evaluation.

This arrangement makes it possible to determine whether it is a lens suitable for a user, or makes it possible to select a suitable lens from among a plurality of lenses, or makes it possible to objectively evaluate a lens.

More specifically, it is possible to evaluate the evoked activity based on a value obtained by measuring a visual evoked field. Additionally, it is possible to evaluate the evoked activity based on a value obtained by measuring a visual evoked potential. A brain's evoked activity generates the change of a slight electric current in a specific part of the brain, and therefore the condition of a change in the activity of the brain's visual cortex evoked when a visual stimulus is given is understood by measuring this change of the slight electric current as a change in magnetic field (magnetic flux density) or in electric potential (voltage) with the lapse of time. Hence, it is possible to make a lens evaluation concerning a to-be-evaluated lens based on a measurement result of the evoked activity of the specific part of the brain's visual cortex. The present invention is made to measure the evoked activity of the brain although a voluntary brain activity that is voluntarily performed and an evoked brain activity that is evoked in response to a stimulus are mentioned as the brain activity. It becomes possible to analyze the activity of a specific part of the brain responding to a stimulus by measuring an evoked activity not by a voluntary activity, and therefore it is possible to measure a difference between slight lens conditions.

Additionally, in the evaluation of the evoked activity of the brain's visual cortex, time from when a visual stimulus to evoke an activity of a specific part of the brain's visual cortex is presented till when an evoked activity appears can be used as an evaluation index. Additionally, in this case, it is possible to evaluate the fact that earliness in time till when an evoked activity appears is a more desirable spectacle lens condition than lateness. Generally, the brain reacts to a visual stimulus, and therefore a lens that is earlier in time (latency) from when a visual stimulus is received till when a change is caused thereby creates a state in which a user more easily recognizes that stimulus, and it is considered that visual information is efficiently processed in the brain or the retina, etc., and therefore the lens is evaluated as being suitable for the user.

Additionally, in the evaluation of the evoked activity of the brain's visual cortex, the magnitude (amplitude) of an activity evoked by presenting a visual stimulus to evoke an activity of a specific part of the brain's visual cortex can be used as an evaluation index. Additionally, in this case, it is possible to evaluate the fact that largeness in the magnitude of the evoked activity is a more desirable spectacle lens condition than smallness. The reason is that the brain or the retina, etc., reacts to a visual stimulus, and it is considered that a user reaches a state of perceiving visual information more easily in proportion to an increase in the change, and therefore the lens is evaluated as being suitable for the user.

As described above, it is possible to evaluate a lens and select a more suitable lens according to either value or both values of the latency and the magnitude (amplitude) of the evoked activity.

Here, concerning a change in electric potential, it is general to measure visual evoked potential (VEP) with an electroencephalograph. Concerning a change in magnetic field (magnetic flux density), it is general to measure visual evoked field (VEF) with a magnetoencephalograph.

Preferably, an object visually observed to give a visual stimulus is disposed in a visual lower half area. In the visual cortex, visual information presented in the lower half area is transmitted to the upper half of the brain area, whereas visual information presented in the upper half area is transmitted to the lower half of the brain area, with brain creases that are called the calcarine sulcus between the upper half and lower half of the brain area. For example, when a visual stimulus object is disposed in the whole visual area, an electric current flowing to the upper half of the brain area with respect to the calcarine sulcus and an electric current flowing to the lower half of the brain area with respect to the calcarine sulcus become substantially opposite to each other in direction. Therefore, in the measurement of the evoked activity of a brain area that is called a primary visual cortex or a secondary visual cortex existing near the center line of the brain, the brain reaction of the upper half area and the brain reaction of the lower half area are offset, and a measurement result becomes small. Additionally, as a reason therefor, generally, in brain reactions, the activity evoked when visual information is presented in the visual lower half area is greater than the activity evoked when it is presented in the visual upper half area, and is easily measured.

Preferably, an object that gives a visual stimulus consists of a combination of line segments. The reason is that there are cells that detect line segments made up of outlines or lines in a lower-level visual cortex, such as the primary visual cortex or the secondary visual cortex, and therefore the brain activity can be evoked in a specific brain part by allowing a subject to visually observe the visual stimulus. Additionally, there are cells that recognize high spatial frequencies in a lower-level visual cortex, such as the primary visual cortex or the secondary visual cortex. Line segments area stimulus object having the highest spatial frequencies, and therefore the reason is that it is possible to evoke the activity of a lower-level visual cortex, such as the primary visual cortex or the secondary visual cortex.

Preferably, the visual stimulus object is presented at a peripheral part away from a fixation point to which attention of the subject is paid when the subject is allowed to visually observe the visual stimulus object. The reason is that there is a case in which the activity evoked by the visual stimulus object presented near the fixation point is observed more than two to four times as largely as the activity evoked by the visual stimulus object presented at the peripheral part. Therefore, preferably, when the subject is allowed to visually observe the visual stimulus object, the visual stimulus object is not presented within a visual angle of 8 degrees from the fixation point to which attention of the subject is paid, excluding the fixation point. This makes it possible to evaluate the lens performance of a lens peripheral part, not a slight refraction state of the lens center.

The reason for evaluating the lens performance of the lens peripheral part is that the lens performance is determined according to how the aberration is disposed at the lens peripheral part particularly in the design of a progressive power lens, and how to remove the aberration from the optical center to the lens peripheral part is important in the design of an aspherical lens, and therefore a desire to evaluate the lens peripheral part is high. Additionally, the reason is that, when the visual stimulus object is presented at a periphery in a state in which the attention of a subject is being paid to the fixation point to which the attention of the subject is paid when the visual stimulus object is visually observed, a brain reaction occurs in a lower-level visual cortex, such as the primary visual cortex or the secondary visual cortex, earlier than an ocular movement occurs after the visual stimulus object is presented, and therefore it becomes possible to evaluate a peripheral vision to which visual attention is not paid.

It is possible to allow an object that gives a visual stimulus to consist of a combination of chromatic colors. The reason is that objects (seen through a lens) seen in daily life are made up of colorful chromatic colors, and therefore chromatic colors of a visual stimulus object make it possible to evaluate the evoked activity of a specific part of a brain's visual cortex or the like concerning a visual stimulus that is closer to that of daily life.

Additionally, if an object to give a visual stimulus is set as a contrast that is obtained by differences in brightness and in color between adjoining areas, it is possible to evaluate the evoked activity of the brain's visual cortex or the like evoked by this contrast. A contrast is shown by a difference in brightness or in color between adjoining areas, and therefore there is a case in which line segments that are not painted out are used not only as a visual stimulus object having spatial frequencies or line segments but also as a visual stimulus object having a contrast. Preferably, when the visual stimulus object used when the visual sense is stimulated by a contrast is set as a combination of chromatic colors, the color of the contrast to be evaluated is selected from scenery, images, or video pictures, etc., having the contrast to be evaluated. The reason is that this makes it possible to evaluate a contrast concerning a color seen in daily life through lenses.

Preferably, in the foregoing, the evoked activity of the primary visual cortex or of the secondary visual cortex is separated from the evoked activity of the brain's visual cortex, and the evoked activity, which has been separated therefrom, of the primary visual cortex or of the secondary visual cortex is evaluated. To separate the evoked activity of the primary visual cortex or of the secondary visual cortex from the evoked activity of the brain's visual cortex is to measure data that has been separated by analyzing a measurement result or by devising a measurement method. For example, in order to separate it therefrom by analyzing a measurement result, there is a method in which a plurality of signal sources are assumed as existing in the brain and are analyzed by use of a multi-signal-source analysis, and, based on its results, the activity of the primary visual cortex or of the secondary visual cortex is analyzed. Additionally, in order to separate it therefrom by devising a measurement method, there is a method in which measurement results of a sensor pair near the primary visual cortex or the secondary visual cortex are selected and analyzed in measurement that uses a magnetoencephalograph, or a method in which electrodes are disposed near the primary visual cortex or near the secondary visual cortex, for example, at Oz, O1, O2, etc., in the international 10-20 electrode system in measurement that uses an electroencephalograph.

Information by the visual stimulus of the brain is transmitted as follows. First, light that has entered from eyes reaches the retina, and is then converted into an electric stimulus, and reaches the primary visual cortex existing in the occipital lobe through the optic nerve. Visual information that has reached the primary visual cortex is divided into that of a belly-side path and that of a back-side path, and, in the belly-side path, is transmitted to higher-level brain parts while the information that has reached the primary visual cortex is processed sequentially in the secondary visual cortex and the tertiary visual cortex in the brain. In the back-side path, the information that has reached the primary visual cortex is transmitted to the head vertex while being processed in the sixth visual cortex.

Heretofore, a pattern reversal stimulus that guides a P100 component as a brain reaction deriving from the primary visual cortex is clinically used in ophthalmology or the like. The pattern reversal stimulus is a stimulus developed by employing the fact that neurons of the brain's visual cortex are insensitive to a stimulus given by uniform irradiation of the retina, and are highly sensitive to a visual stimulus given by a figure that has outlines or contrast, and is characterized in that it is unsusceptible to a difference in latency between individuals or to a difference between refraction states because comparatively earlier components are evoked in the process step of visual information. More specifically, a subject is allowed to repeatedly gaze at an inverted checkered pattern, and, as a result, a P100 component deriving from the primary visual cortex is guided. The P100 component is an indexed reaction named from the fact that time from when a visual stimulus is received till when a change occurs in response to the stimulus is roughly 100 milliseconds.

However, there is a case in which the P100 component by the pattern reversal stimulus is not easily distinguished in a person who easily releases alpha ($\alpha$) wave, and there is a case in which a person does not easily release it. Additionally, in the pattern reversal stimulus, the entire retina cell is irradiated with light evenly in each half of its area, and therefore the retina cell is irradiated with light of the visual stimulus object during half the period of measurement time. If cells are allowed to repeatedly act with short intervals of time, an afterimage will occur without recovering the cells so as to reach their initial states, and the brain reaction will also gradually become weak, and therefore there is a case in which it is difficult to obtain a strong reaction in the pattern reversal stimulus. On the other hand, if the visual stimulus object consists of a combination of line segments as in the present invention, the retina cell will be irradiated with light only at the place of the line segments, and it is easy to control the amount of irradiation of light according to the number of line segments or according to the thickness of a line segment or according to brightness, and therefore it becomes possible to analyze a difference in evoked activity even under a slight lens condition under which it is difficult to perform measurement in the pattern reversal stimulus. Preferably, at this time, the visual stimulus object consists of at least two kinds of visual stimulus objects that are equal to each other in total length of the line segments of which each visual stimulus object is formed, and the at least two kinds of visual stimulus objects are alternately presented. The reason is that it is possible to make the irradiation time of light with which a specific retina cell is irradiated even shorter, and it is possible to reduce the afterimage.

Preferably, when an electroencephalograph is used for a method for evaluating an evoked activity, a change in potential that is caused by giving a predetermined visual stimulus is immediately after a P100 component, and an evoked activity that is opposite in peak extreme value to the P100 component is measured. Specifically, this is, for example, an N130 component in the embodiment. The reason is that, in this brain reaction, the measurement result often varies while reflecting a slight lens difference unlike the P100 component, and therefore it shows a brain reaction that appropriately reflects a difference in the lens refraction state when different to-be-evaluated lenses are worn.

In the representation of these components, the numerals denote time (millisecond) from when a visual stimulus is received till when a brain reaction occurs, and the occurrence timing also varies according to the brightness or the contrast of the visual stimulus object, and therefore the numerals merely denote that "it occurs in a time zone therearound" in a standard condition, and, when the occurrence timing varies according to the condition of the visual stimulus object from the standard condition, the occurrence timing that has not yet varied is named to determine its component. As examples of this naming, there are a P300 and the like that relate to a cognitive judgment in addition to the P100.

Additionally, a difference made when lenses are worn in the visual evoked activity can be easily discriminated by lowering the brightness or the contrast of an object visually observed to give a visual stimulus, and therefore it is preferable to perform an adjustment in accordance with a measurement target. It is possible to adjust the brightness by adjusting the thickness or density of a line segment of a stimulus and to adjust the contrast by adjusting the brightness of a measurement environment or by adjusting a difference in brightness between the line segment and a part excluding the line segment of the stimulus. When an object visually observed to give a visual stimulus is made up of chromatic colors, it is possible to adjust the contrast by, for example, a combination of the color of the line segment of the stimulus and colors other than that of the line segment.

An aspherical lens having its peripheral part whose shape is changed little by little can be mentioned as an example of a spectacle lens to be evaluated. The lens diopter power may be changed little by little from the center to the peripheral edge. The aspherical lens is not limited to a monofocal lens. A progressive power lens whose lens shape is changed little by little is also permissible. Particularly when a visual stimulus object is disposed in a visual lower half area, the surface shape or the optical change of the progressive power lens is larger in the lower part of the lens than in the upper part, and therefore this lens is suitable. It is also possible to select a lens whose spectral transmittance (spectral distribution) is changed by optical absorption or optical reflection, etc. The spectral transmittance denotes the wavelength distribution of light that passes through the lens, which shows how many percent of light passes through the lens in each wavelength of light, and it is possible to change the contrast or the dazzle when seen through a lens by changing the spectral transmittance.

Preferably, spectacle lenses are designed by using the method for evaluating spectacle lenses by an evoked activity of a brain's visual cortex or the like. To design spectacle lenses is to determine design information of lenses, such as progressive power lenses or aspherical lenses, by controlling the lens shape of the spectacle lens and controlling refracting power or the like at each point of the lens, and is to determine design information of lenses, for example, by controlling optical absorption or optical reflection of light on the spectacle lens or of light inside the spectacle lens and controlling the spectral transmittance (spectral distribution) of the lens. For example, the evaluation of a spectacle lens by the evoked activity of a brain's visual cortex or the like is performed concerning a plurality of to-be-evaluated lenses, and it is possible to obtain lens design information of a to-be-evaluated lens and an evaluation value of the spectacle lens by the evoked activity of the brain's visual cortex or the like corresponding thereto. It is possible to calculate optimal lens design information by analyzing a change in the evaluation value caused by a change in the lens design information from corresponding lens design information and evaluation values of the plurality of lenses. Preferably, lens design information and calibration curves of evaluation values are beforehand created, and lens design information is calculated from evaluation values measured by correlating measured evaluation values with the calibration curve.

Effects of the Invention

In each example mentioned above, it becomes possible to objectively evaluate a spectacle lens suitable for a user by measuring the evoked activity of a specific part of the brain's visual cortex.

DESCRIPTION OF EMBODIMENTS

Specific embodiments of the present invention will be hereinafter described with reference to the drawings.

Embodiment 1

1. Method for Measuring Evoked Activity

Figure 1:
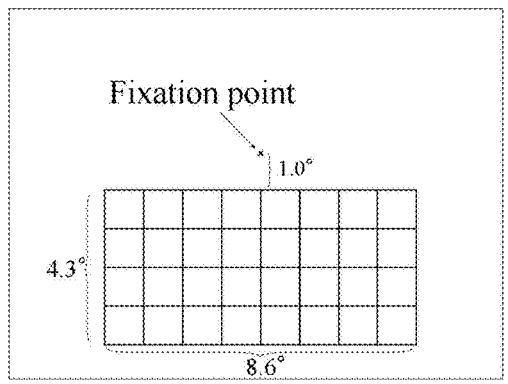
FIG. 1 A front view of one example of a stimulus object that stimulates a visual sense in Embodiment 1. The angle in FIG. 1 designates a visual angle.

A stimulus object that is a hemi-visual field lattice having a low brightness (0.16 cd/m$^2$) and that is presented in a visual lower half area shown in, for example, FIG. 1 (FIG. 1 actually becomes a reverse image in visual observation) at a visual distance of 2 m is repeatedly presented at a stimulus of 250 milliseconds (hereinafter, referred to as ms) with stimulus-to-stimulus intervals of 500 ms while allowing a subject to gaze at a fixation point. In other words, the stimulus object is blinked such that the fixation point is presented for 250 ms, and then FIG. 1 is presented for 250 ms, and the fixation point is presented for 250 ms. In the present embodiment, the brightness of the stimulus object is adjusted so that the peak of the visual evoked field can be satisfactorily recognized even if it is S+4 D in a preliminary experiment. The viewing angle of this lattice is 4.3 degrees× 8.6 degrees.

A visual evoked field (VEF) is measured by allowing a subject to wear a to-be-evaluated lens having each diopter power of S+0 D, S+1 D, S+2 D, or S+4 D from the plus side in addition to a regular diopter power on the condition that the lens diopter power of spectacles now worn by the subject is defined as the regular diopter power. In the measurement, non-magnetic lenses and non-magnetic frames are used in a magnetic shield darkroom, and a 306-channel magnetoencephalograph (Vector-view, ELEKTA Neuromag, Helsinki, Finland) is used. The 306-channel magnetoencephalograph is composed of 102-channel magnetometers serving as magnetic sensors disposed in a dispersion manner inside a helmet-shaped main body and 102-pair (204-channel) gradiometers. In the 306-channel magnetoencephalograph, the evoked field of the gradiometer at a predetermined measurement position of the brain is acquired by allowing the subject to put its main body on the head, and is set as an analysis object.

Figure 2:
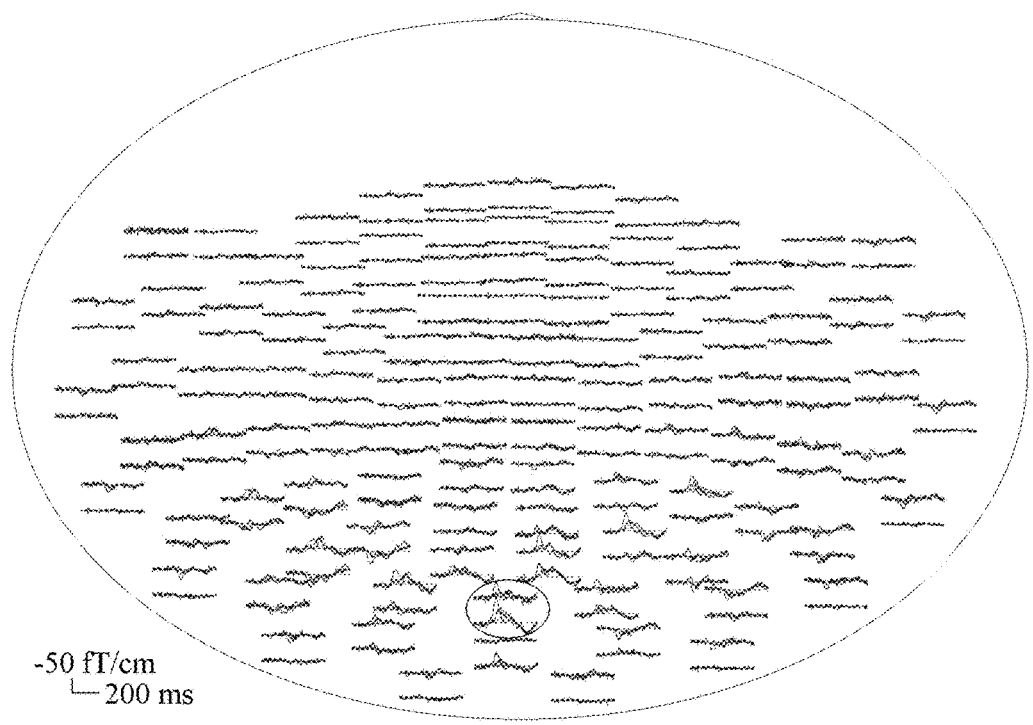
FIG. 2 One example of a measurement result in which each measurement position of the brain in Embodiment 1 and a change in the acquired magnetic flux density are arranged to be correlated with each other.
Figure 3:
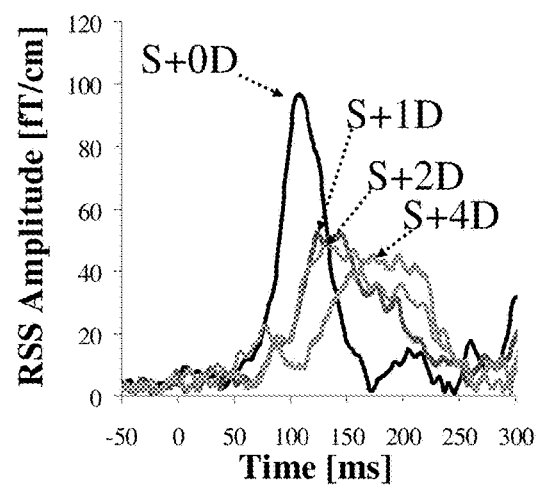
FIG. 3 A graph showing a relationship between a root-sum-square value (RSS value) and time concerning a change in magnetic flux density.
Figure 4:
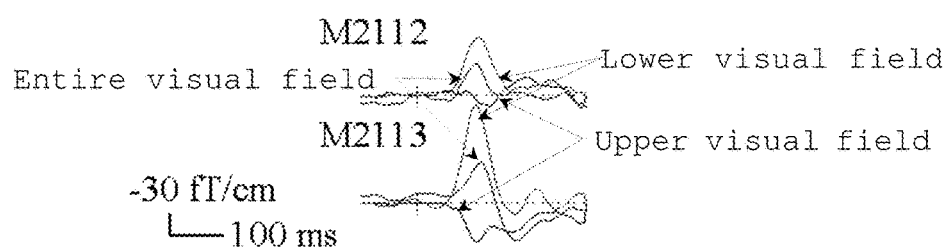
FIG. 4 A graph in which one example of a waveform (graph) at the position of a round mark of FIG. 2 is enlarged.

The thus arranged magnetoencephalograph makes it possible to obtain an evoked field, such as that of FIG. 2, as a measurement result. FIG. 2 is a schematic view in which each measurement position of the brain to which a gradiometer is adjacent and a change in the magnetic flux density obtained thereby are arranged to be correlated with each other. In the figure, the upper side is the face side when the head is viewed planarly. Herein, the waveform of a sensor that is most strongly obtaining evoked responses near an occipital lobe is selected in FIG. 2 (position of the round mark of FIG. 2). The position of this round mark is near a primary visual cortex. FIG. 4 shows one example in which the waveform (graph) at the position of the round mark of FIG. 2 is enlarged concerning a subject. M2112 and M2113 are codes, each showing a measurement position at the position of the round mark. When a comparison in the magnitude of the change is made between a case in which an object to be viewed at this measurement position resides in the hemi-visual field and on the upper visual field side, and, likewise, a case in which it resides in the hemi-visual field and on the lower visual field side, and, likewise, a case in which it resides in the entire visual field, the magnitude of the change is obviously large when the object to be viewed is placed on the lower visual field side. Therefore, in Embodiment 1, the subject is allowed to gaze at the stimulus object of a hemi-visual field lattice as shown in FIG. 1. Herein, concerning a change in the magnetic flux density at the position of the round mark, each value of a pair of upper and lower gradiometers is squared, and the square root of an added value (square root of sum of squares (RSS)) is calculated, and, as a result, a waveform for evaluation is obtained (FIG. 3). Hereinafter, this waveform for evaluation is referred to as an RSS waveform.

2. Evaluation Method

The aforementioned measurement method was performed in Embodiment 1 concerning three subjects. The graph of the RSS waveform of one (Subject 1) of the three subjects is FIG. 3. As shown in FIG. 3, in the waveform calculated above, the evoked activity seen near 100 ms is an M100 component in the regular diopter power (0 D). In this case (Subject 1) of FIG. 3, it is understood that the diopter power deviates from the regular diopter power to the plus, and hence the amplitude of the peak of the M100 component becomes small, and the latency becomes late, and therefore the regular diopter power (0 D load) is desirable. Measurement results of the latency of the three subjects are shown in Table 1 concerning the latency of the M100 component.

In Subject 1, it is understood that the latency becomes later in proportion to an increase of plus load diopter power, and therefore the lens state of 0 D is desirable. In Subject 2, it is suggested that 1 D is earlier in latency than 0 D, and hence the subject wears lenses that are negatively strong in the regular diopter power (in other words, the subject is in an excessively corrected state). In Subject 3, the M100 component that is expected to appear near 100 milliseconds is late so as to appear in 150 milliseconds. This suggests that the regular diopter power of Subject 3 largely deviates to the plus.

TABLE 1

| | Latency (ms) | | | |
|---|---|---|---|---|
| | 0 D | 1 D | 2 D | 4 D |
| Subject 1 | 106.6 | 124.5 | 131.5 | 166.3 |
| Subject 2 | 107.6 | 103.6 | 109.6 | 129.5 |
| Subject 3 | 154.4 | 162.3 | 170.3 | 170.3 |

Embodiment 2

Embodiment 2 is a variation that uses the measurement method of Embodiment 1. Only the evaluation method will be hereinafter described.

Figure 5:
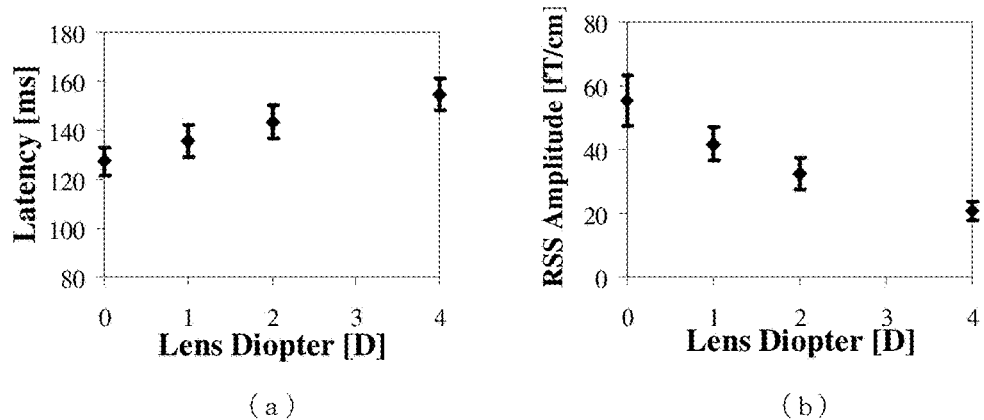
FIG. 5 (a) of FIG. 5 is a graph showing a relationship between the lens diopter power of a mean value of ten subjects and the latency of an M100 component, and, likewise, (b) of FIG. 5 is a graph showing a relationship between the lens diopter power and the amplitude of the M100 component in Embodiment 2.

In Embodiment 2, concerning ten subjects, RSS waveforms were calculated, and the latency and the amplitude of the M100 component of each lens diopter power were calculated. FIG. 5(*a*) is a graph showing a relationship between the latency and lens diopter power added to the regular diopter power, and FIG. 5(*b*) is a graph showing a relationship between the amplitude and lens diopter power added to the regular diopter power. The average of the ten subjects and an average error are shown by an error bar. The earlier the latency is, the more suitable the lens becomes, and the greater the amplitude is, the more suitable the lens becomes.

Thus, it is understood that the latency and the amplitude make it possible to evaluate an objective wearing state. Additionally, a delay of about 10 milliseconds in the latency is seen with respect to the regular diopter power under the 1 D load condition, and therefore it is understood that the wearing state can be objectively evaluated even if the difference in diopter power is smaller than, for example, 0.25 D. Still additionally, it is also possible to measure a smaller difference in diopter power by lowering the brightness or the contrast of a stimulus object.

Embodiment 3

1. Method for Measuring Evoked Activity

For example, a lattice-shaped stimulus object as shown in FIG. 1 is repeatedly presented for each period of a stimulus of 250 milliseconds with stimulus-to-stimulus intervals of 500 milliseconds at a visual distance of 1.5 m in each of the entire visual field, the upper visual field, and the lower visual field while allowing the subject to gaze at a fixation point in a darkroom. FIG. 1 is an example of a stimulus in the lower visual field. Reference electrodes are attached to both ears, and an earth electrode is attached to the forehead, and the evoked potential of Oz of the international 10-20 electrode system is measured with an electroencephalograph. The subject is allowed to wear a plurality of to-be-evaluated lenses that differ in lens diopter power from each other on the condition that the lens diopter power of spectacles now worn by the subject is defined as the regular diopter power, and the visual evoked potential (VEP) is measured.

2. Evaluation Method

Figure 6:
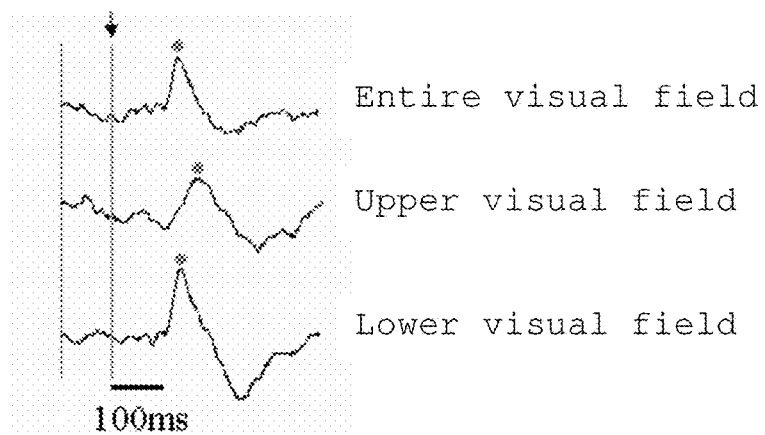
FIG. 6 A graph showing a relationship between visual evoked potential measured concerning Subject 4 and time in Embodiment 3.
Figure 7:
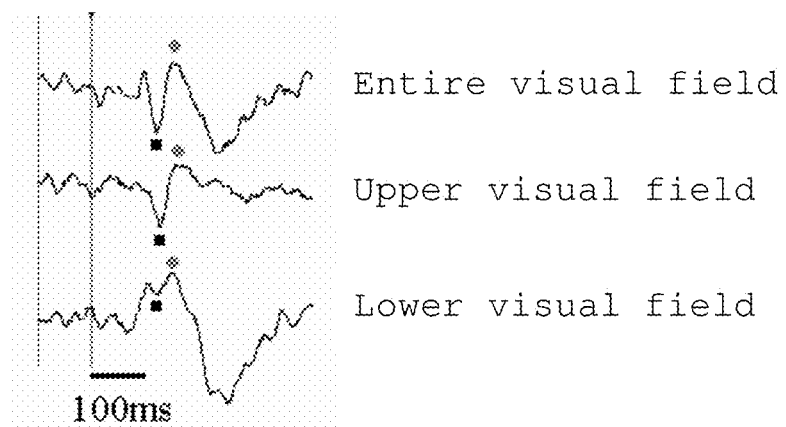
FIG. 7 A graph showing a relationship between visual evoked potential measured concerning Subject 5 and time in Embodiment 3.

FIG. 6 is a graph of a measurement value concerning a certain to-be-evaluated lens obtained by the aforementioned measurement method concerning Subject 4. FIG. 7 is a graph of a measurement value concerning a certain to-be-evaluated lens obtained by the aforementioned measurement method concerning Subject 5.

In these graphs of FIG. 6 and FIG. 7, the abscissa axis represents time (ms), and the ordinate axis represents electric potential (microvolt). The reference potential is defined as an average in potentials for 100 ms while going back 100 ms from stimulus presentation, and in these figures, the upward direction is defined as a minus (negative) direction, and the downward direction is defined as a plus (positive) direction.

In the graph of FIG. 6, a negative peak (i.e., peak to which a ● mark is given) near 130 ms is an N130 component. Likewise, in the graph of FIG. 7, a negative peak near 130 ms is an N130 component. Additionally, in the graph of FIG. 7, a P100 component (i.e., peak to which a ■ mark is given) deriving from the primary visual cortex is seen.

Figure 8:
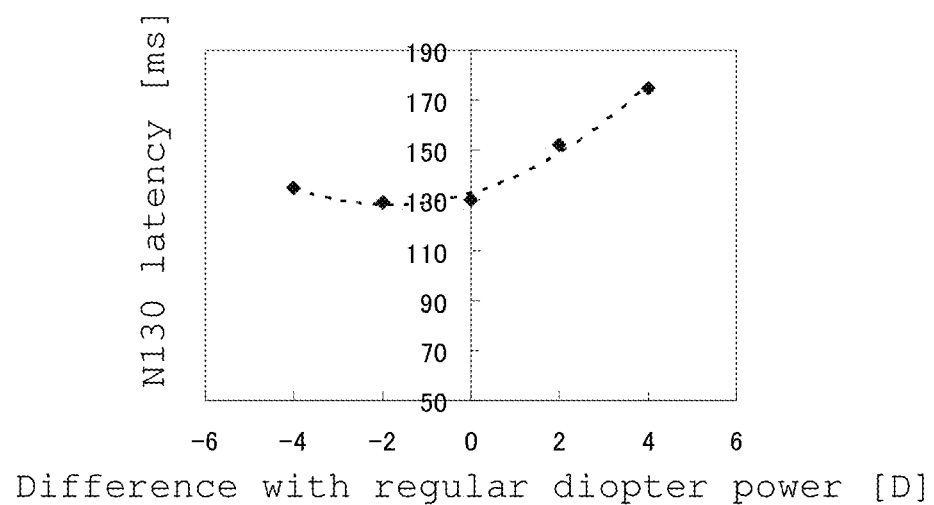
FIG. 8 A graph showing a relationship between different to-be-evaluated lenses that are worn by Subject 4 and the latency of N130 in Embodiment 3.

Concerning Subject 4, the N130 component appears more strongly and more sharply in the lower visual field than in the entire visual field and than in the upper visual field. In Subject 4, although the P100 component deriving from the primary visual cortex is hardly observed, the N130 component appears vividly, and therefore it is possible to stably observe it even if the P100 component is hard to appear. FIG. 8 is a graph showing a relationship between to-be-evaluated lenses worn by Subject 4 that are different from each other every 2 D difference in lens diopter power and the latency of the N130 component. Although this N130 was 130 milliseconds in the regular diopter power (0 D condition) of Subject 4, it was 152 milliseconds in the S+2 D load, it was 175 milliseconds in the S+4 D load, it was 129 milliseconds in the S −2 D load, and it was 135 milliseconds in the S −4 D load. In this case, it is possible to judge that slightly minus diopter power is preferable to the regular diopter power. After making this judgment, the brightness and the contrast of the index are made even smaller, and a comparison is made between even smaller diopter power errors, and, as a result, it is possible to derive lens conditions appropriate for Subject 4.

Both the P100 component and the N130 component are observed in Subject 5. In Subject 5, a comparatively large P100 component is observed in an entire visual field stimulus and in an upper visual field stimulus, and yet, in some subjects, it is difficult to identify this P100 component as in Subject 4, and therefore it is not best to use this as an index for lens evaluation with respect to various subjects. On the other hand, when a lower visual field stimulus is presented, the N130 component appears as a greater peak than the P100 component, and therefore it is possible to identify the latency and the amplitude of the N130 component in some subjects, such as Subject 5, in whom the P100 component easily appears, and it is possible to evaluate the lens performance by using the N130 component presented as a stimulus in the lower hemi-visual field even if the subject is a person in whom the P100 component easily appears or a person in whom the P100 component does not easily appear.

Embodiment 4

1. Method for Measuring Evoked Activity

Figure 9:
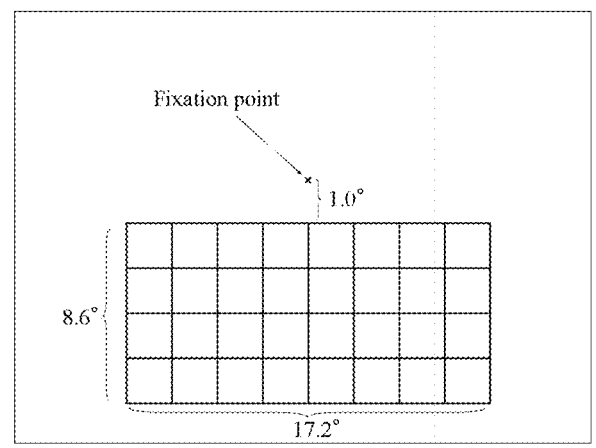
FIG. 9 A front view of one example of a stimulus object that stimulates a visual sense in Embodiment 4.

A lattice-shaped stimulus object low in brightness to be presented in the visual lower half area as shown in, for example, FIG. 9 is repeatedly presented at a visual distance of 0.5 m for each period of a stimulus of 250 milliseconds with stimulus-to-stimulus intervals of 500 milliseconds while allowing a subject to gaze at the fixation point in a dim room (FIG. 9 actually becomes a reverse image in visual observation). Reference electrodes are attached to both ears, and an earth electrode is attached to the forehead, and the evoked potential of Oz of the international 10-20 electrode system is measured with an electroencephalograph. On the condition that the lens diopter power of spectacles now worn by the subject is defined as the regular diopter power, the subject is allowed to wear a plurality of to-be-evaluated lenses (progressive power lenses), in which the additional diopter power is gradually changed from the upper part toward the lower part of the lens, from above the lens of the regular diopter power, and the visual evoked potential (VEP) is measured.

Figure 10:
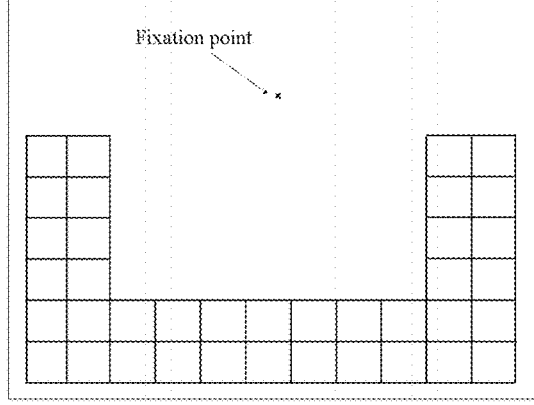
FIG. 10 A front view of one example of a stimulus object that stimulates a visual sense in Embodiment 4.

It should be noted that another index, such as that of FIG. 10, is desirable particularly when only the peripheral part is evaluated (FIG. 10 actually becomes a reverse image in visual observation). This makes it possible to reduce the influence of a brain reaction received by the visual stimulus object near the fixation point, and makes it possible to evaluate only the peripheral part of the lens (i.e., peripheral observation).

2. Evaluation Method

Embodiment 4 is an evaluation example of the peripheral part of the lens presenting the visual stimulus object of FIG. 10.

In a comparison between a case in which condition 1 is applied in which a change of 0.5 D is made from the upper part toward the lower part of the lens with respect to the regular diopter power of Subject 6 (i.e., the diopter power for far vision is 0 D and the additional diopter power is 0.5 D), a case in which condition 2 is applied in which a change of 1.0 D is made with respect thereto, and a case in which condition 3 is applied in which a change of 2.0 D is made with respect thereto, the latency of N130 was 128 milliseconds in condition 1, the latency of N130 was 130 milliseconds in condition 2, and the latency of N130 was 135 milliseconds in condition 3.

From this fact, it is understood that, in Subject 6, the lens condition of condition 1 is desirable in a short distance of 50 cm.

Embodiment 5

1. Method for Measuring Evoked Activity

Embodiment 5 is a variation that uses the measurement method of Embodiment 4. On the condition that the lens diopter power of spectacles now worn by the subject is defined as the regular diopter power (for example, the regular diopter power of this subject is set to be S −5.00 D), the subject is allowed to wear a plurality of to-be-evaluated lenses (monofocal lenses), in which the diopter power and the astigmatism (astigmatic component) of the lens are gradually changed from the center of the lens toward its periphery, and the visual evoked potential (VEP) is measured while giving the same visual stimulus as in Embodiment 4.

Figure 11:
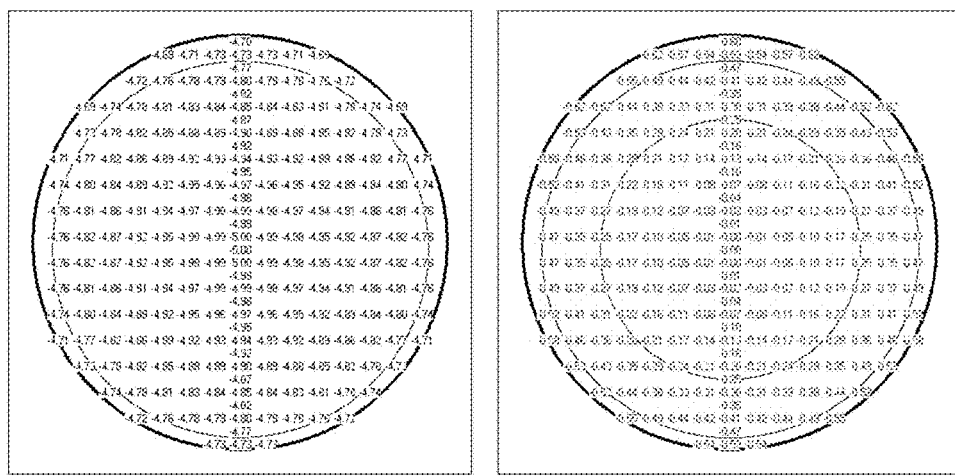
FIG. 11 A distribution view showing the diopter power distribution of a monofocal lens (left-hand view) and the astigmatism distribution (right-hand view) in Embodiment 5.
Figure 12:
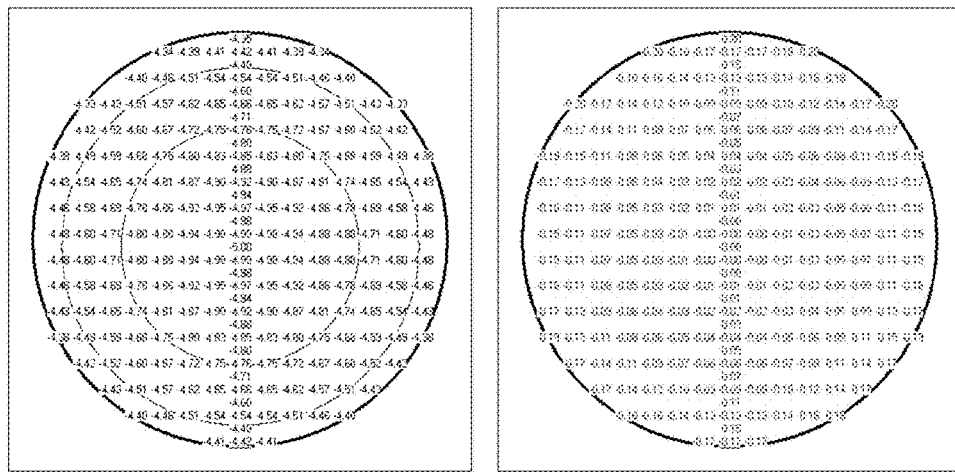
FIG. 12 A distribution view showing the diopter power distribution of a monofocal lens (left-hand view) and the astigmatism distribution (right-hand view) in Embodiment 5.

FIG. 11 and FIG. 12 are design examples of monofocal lenses having the same center diopter power (S −5.00 D), respectively. As shown here, in the monofocal lens, the diopter power and the astigmatism (astigmatic component) of the lens change from the center of the lens toward its periphery. In the design example of FIG. 11, the astigmatism (astigmatic component) makes a change of about −0.50 D, and the diopter power makes a change of about S+0.30 D from the center of the lens toward its periphery. On the other hand, in the design of FIG. 12, although the astigmatism makes a change of about −0.20 D which shows that the astigmatism is restrained from becoming worse than in Design 1, the diopter power makes a change of about 0.60 D so as to deviate to the plus side which shows that the diopter power error is large.

2. Evaluation Method

In lens design, the error in diopter power and the error in astigmatism are in a trade-off relationship in which if either one of the two is made smaller, the remaining one will be made larger. Additionally, there are personal preferences, and lens design that makes a person seem desirable depends on individuals some of whom like to see it clearly, and some of whom like to see it boldly, and some of whom like to see it neatly. Therefore, it is difficult to derive the type of the best design only from optical simulation calculations.

The N130 is obtained by the aforementioned measurement method, and, as a result, its latency or its amplitude is used as an index, and hence, concerning differences in design between monofocal lenses, it becomes possible to select a desirable design for a user. For example, the design of FIG. 11 that is small in the diopter power error and the design of FIG. 12 that is small in the astigmatism error are compared with each other with respect to Subject 6 whose right eye is S −4.00 C −1.00 AX170 and whose left eye is S −4.00 C −1.00 AX15 according to the same measurement method as the evaluation of peripheral observation (lens peripheral part) in Embodiment 4. (At this time, the aspherical amount is adjusted according to the diopter power of Subject 6. Additionally, the aspheric surface is set to meet the astigmatism according to a well-known aspherical astigmatism correction technique.) As a result, from the fact that the N130 measured by Oz was 135 ms in the design of FIG. 11 that is small in the diopter power error and was 140 ms in the design of FIG. 12 that is small in the astigmatism error, it is understood that, for Subject 6, it is important to be small in the diopter power error of the peripheral part as in the design of FIG. 11. Based on this finding, it is possible to design spectacle lenses by using the evaluation value of the spectacle lens (in this Embodiment 5, the latency of the N130) based on the evoked activity of the brain's visual cortex or the like. Additionally, concerning the design having an intermediate lens shape between the design of FIG. 11 and the design of FIG. 12, the N130 was calculated in Subject 6, and, as a result, it was 134 ms. From the fact that it was 135 ms in the design of FIG. 11, it was 134 ms in the intermediate design, and it was 140 ms in the design of FIG. 12, it is possible to infer that the best design exists near the middle between the design of FIG. 11 and the intermediate design, and, as a result, the parameter of lens design information is determined. This evaluation is repeatedly performed, and, as a result, it is possible to design spectacle lenses by use of the latency of the N130.

Concerning the delay of the latency, the delay is made even longer by reducing the brightness of a visual stimulus object or by lowering its contrast, and thus it is possible to measure a difference in lens performance in the same way as in the other embodiments.

Embodiment 6

Embodiment 6 is a variation that uses the measurement method of Embodiment 1. The evoked activity of the brain's visual cortex is separated into the evoked activity of the primary visual cortex and the brain activities of the secondary and tertiary visual cortices that are higher-level ones than the primary visual cortex by use of dipole estimation from a change in the magnetic flux density obtained by the gradiometer in Embodiment 1.

Figure 13:
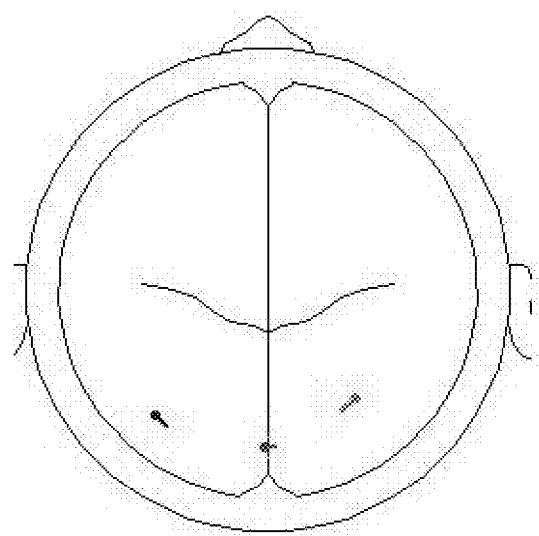
FIG. 13 A descriptive view that describes the positions of separated evoked activity sources in Subject 7 and the direction of electric current flowing through each activity source in Embodiment 6.
Figure 13:

FIG. 13 is one example of a result obtained by separating the evoked activity source in Subject 7. FIG. 13 is a plan view of the brain, which has been cut in a horizontal direction, seen from above, and the mark indicates the position of the activity source and a direction in which an electric current flows from the activity source. An upward activity near a center line shows an activity of the primary visual cortex (V1), and inward left and right activities show activities of the tertiary visual cortex (V3). In Subject 7, although the secondary visual cortex was not identified because the activity of the secondary visual cortex was weakly observed, it is possible to set the activity source of the secondary visual cortex at a position between the primary visual cortex and the tertiary visual cortex and to analyze the evoked activity of the secondary visual cortex. The primary visual cortex and the tertiary visual cortex (also the secondary visual cortex if the secondary visual cortex can be identified) were identified by dipole estimation in this way, and then the evoked activity of each activity source was analyzed.

Figure 14:
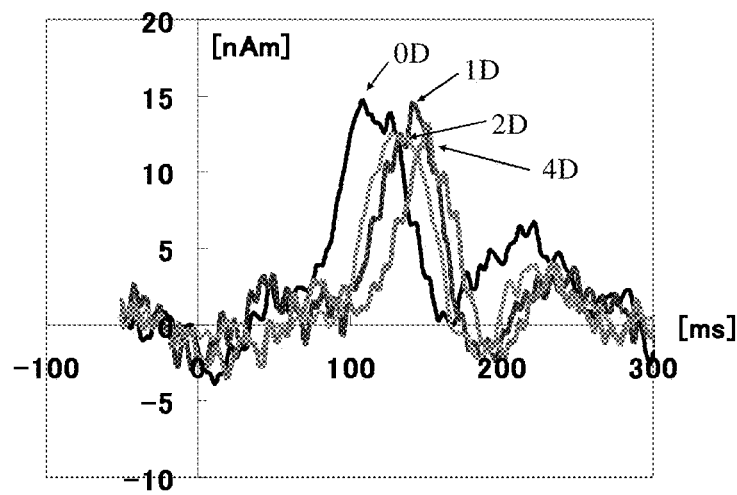
FIG. 14 A graph showing time-dependent changes in signal strength of the separated evoked activity sources of Subject 7, (a) of FIG. 14 showing a change by lens diopter power of the evoked activity of a primary visual cortex (V1), (b) of FIG. 14 showing a change by lens diopter power of the evoked activity of a tertiary visual cortex.
Figure 14:
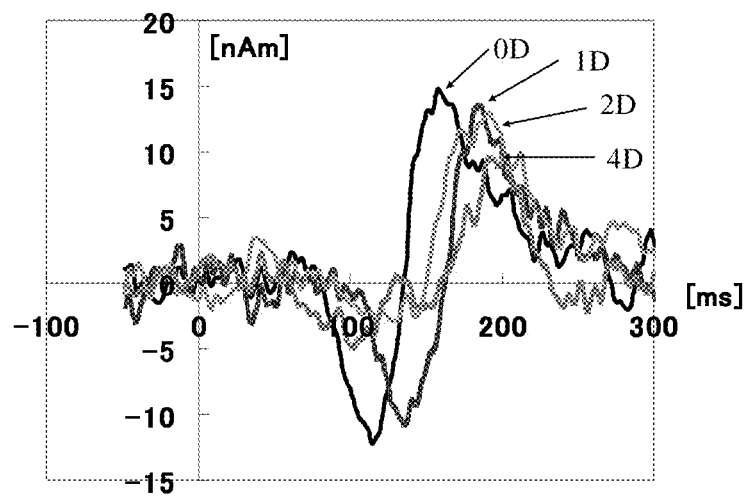

FIG. 14(a) and FIG. 14(b) each show a change in the activity source that generates a change in the magnetic flux density separated in Subject 7, (a) being an evoked activity of the primary visual cortex (V1), (b) being an evoked activity of the tertiary visual cortex. The abscissa axis represents time from visual stimulus presentation, and the ordinate axis represents the signal source strength (whose unit is nanoampere meter) of an activity source that generates a change in the magnetic flux density.

According to analysis of FIG. 14(a), the peak of about 15 nAm is observed at about 100 ms in the regular diopter power (0 D). This is an evoked activity of the primary visual cortex that generates the M100 component used for analysis in Embodiments 1 and 2. It is understood that this evoked activity of the primary visual cortex becomes later in latency 150 ms from about 100 ms when the diopter power deviates to the plus than in the regular diopter power (0 D). On the other hand, according to analysis of FIG. 14(b) that is the evoked activity of the tertiary visual cortex, it is 150 ms in 0 D, and it is 200 ms in 4 D, and hence the latency changes when the diopter power deviates. Although the method for analyzing the M100 component in Embodiments 1 and 2 or the method for analyzing the N130 component in Embodiments 3 to 5 analyzes the waveform that is an aggregate of various activities, it becomes possible to make an evaluation by making an analysis after being separated into each brain activity as in Embodiment 6 even if it is a smaller difference in lens refraction.

Embodiment 7

Embodiment 7 is an embodiment that uses "contrast" as a visual stimulus.

The contrast of an image seen through a lens is changed by wearing lenses (e.g., color lenses) that cut specific wavelengths by optical absorption or by optical reflection. However, it is difficult to objectively measure contrast, and therefore a main product-development technique is employed in which a product is designed basically by using spectral transmittance curves, and is subjectively evaluated. Therefore, in Embodiment 7 performed here, a visual stimulus object to evoke the activity of a specific part of the brain's visual cortex is visually observed through a lens that controls spectral transmittance (spectral distribution), and then the evoked activity of the brain's visual cortex is measured when the visual stimulus object is visually observed by the aforementioned to-be-evaluated lens, and the contrast is quantified by evaluating the evoked activity of the brain's visual cortex.

Cells that recognize edges or line segments and cells that recognize high spatial frequencies, in addition to cells that recognize brightness, exist in the primary visual cortex of the brain. When an index shown in, for example, FIG. 16 (this index consists of line segments having light gray and the background having dark gray closer to black) is presented, it is understood that if the activity of the primary visual cortex of the brain is high (in other words, if time is early until an evoked activity appears or if the evoked activity is great), it denotes that a difference between the background and the line segments of FIG. 16 is perceived by the primary visual cortex of the brain, and the stimulus object seen by the subject through the lens has a high contrast.

1. Evoked-Activity Measurement Method and Evaluation Method

Figure 15:
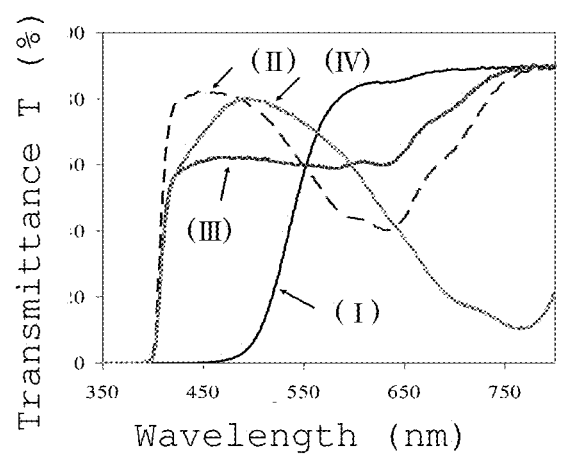
FIG. 15 A graph of spectral transmission (spectral distribution) of a color lens used in Embodiment 7.
Figure 16:
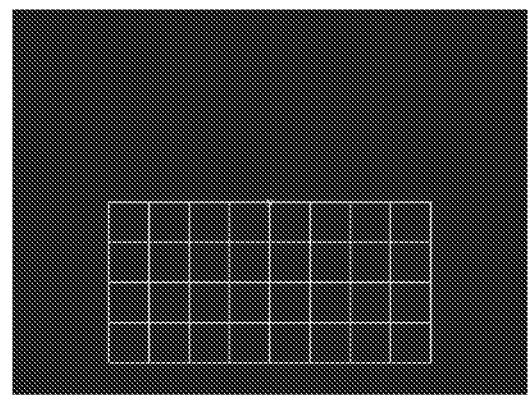
FIG. 16 A front view of one example of a stimulus object that stimulates a visual sense in Embodiment 7.

The subject was allowed to wear color lenses having spectral waveforms (I) to (IV) shown in FIG. 15, and the visual evoked field (VEF) was measured while presenting a lattice-shaped stimulus object having a low brightness and a low contrast presented in the visual lower half area shown in FIG. 16 for each period of a stimulus of 250 ms with stimulus-to-stimulus intervals of 500 ms in a magnetic shield darkroom. In the measurement, non-magnetic lenses and non-magnetic frames were used, and a 306-channel magnetoencephalograph was used. Concerning an analysis, the activity of the primary visual cortex was separated from those of the secondary and tertiary visual cortices by use of dipole estimation, and then the activity of the primary visual cortex was analyzed and evaluated.

Figure 17:
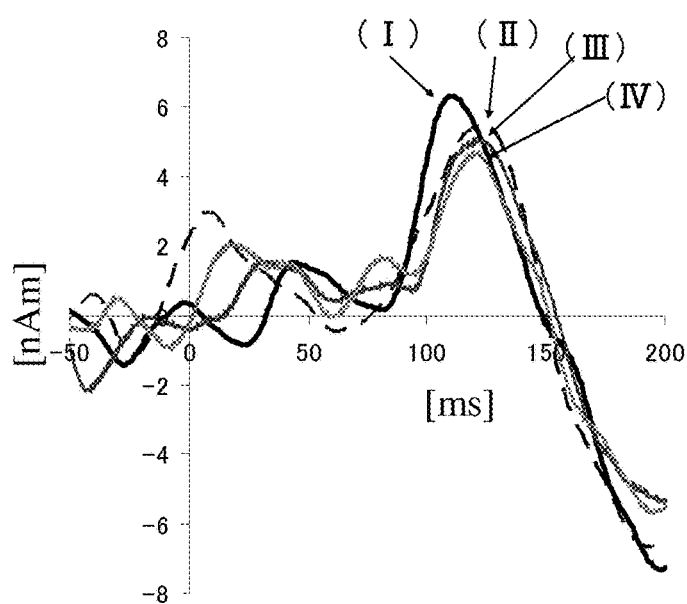
FIG. 17 A graph showing a relationship between a lens and a time-dependent change in signal strength of the activity of a primary visual cortex that has been separated from the activity of the brain's visual cortex or the like of Subject 12 in Embodiment 7.

In Subject 12, the latency of the activity (M100) of the primary visual cortex was (I)<(IV)≈(III)<(II), and, as a result, the contrast rose in lens (I) (FIG. 17). The amplitude also exhibited an increase of about 10% in lens (I), and it was understood that the contrast becomes higher in color (I) among the four colors compared with each other.

On the other hand, the latency of the M100 of Subject 13 was (IV)<(I)≈(II)<(III). It was understood that the contrast becomes higher in lens color (IV) in Subject 2.

If brain reactions used as measurement targets for evaluation are narrowed based on these experimental results, it is also possible to perform measurement while using brain waves in a state in which electrodes are fixed to only are as near the measurement targets although Embodiment 7 mentioned here is based on magnetoencephalograms. For example, in this case, it is possible to evaluate the contrast by means of, for example, a low-contrast visual stimulus object and the evaluation technique of Embodiment 3.

Embodiment 8

Embodiment 8 is also an embodiment using "contrast" as a visual stimulus. The background and the stimulus object (line segments) of FIG. 16 in Embodiment 7 were set to be chromatic colors, and the contrast of a scene closer to daily life was evaluated. Although the contrast of achromatic colors was presented in Embodiment 7, the world of daily life is formed of colorful chromatic colors. Therefore, it is important to evaluate the contrast of chromatic colors.

Figure 18:
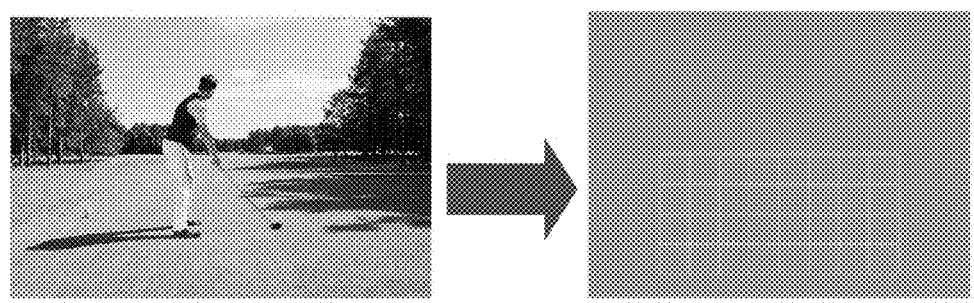
FIG. 18 A descriptive view that describes the use of a yellow-green lattice-shaped stimulus object in which the background is set to be grass green, and the lattice color is set to be yellow on the assumption that this is the grass grain of a golf course in Embodiment 8.

In Embodiment 8, a yellow-green lattice-shaped stimulus in which the background was set to be grass green RGB (157, 172, 85) and in which the lattice color was set to be yellow RGB (216, 203, 119) assuming the grass grain of a golf course as shown in FIG. 18 was presented to Subject 14 for each period of a stimulus of 250 ms with stimulus-to-stimulus intervals of 500 ms.

Figure 19:
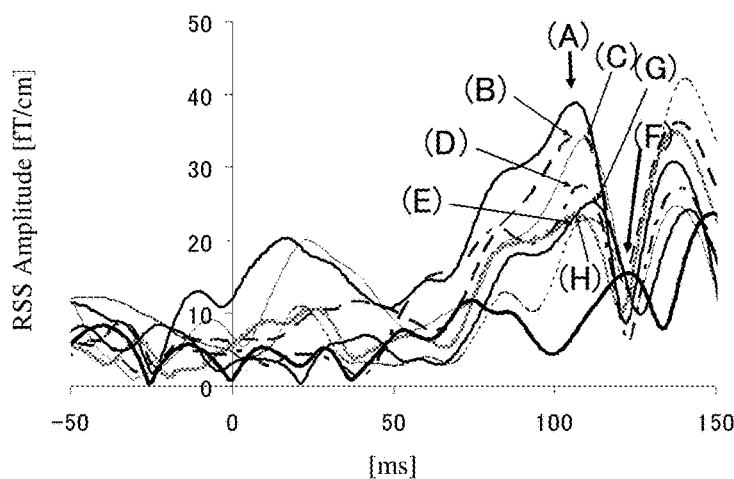
FIG. 19 A graph showing a relationship between a time-dependent change in the root-sum-square value (RSS value) concerning a change in magnetic flux density of the activity of a primary visual cortex of Subject 14 and lenses (A) to (H) that differ in spectral transmission from each other in Embodiment 8.

Subject 14 was allowed to wear color lenses (A) to (H), and measurement was performed at a visual distance of 2 m by use of the 306-channel magnetoencephalograph. Concerning an analysis, the latency and the amplitude of the M100 were calculated by the RSS waveform of the gradiometer pair near V1 according to the same method as in Embodiment 1 (FIG. 19).

Likewise, in this embodiment, it is possible to make an analysis with even higher accuracy by performing dipole estimation with, for example, BESA and by separating the activity of the primary visual cortex from those of the secondary and tertiary visual cortices in the same way as in the other embodiments. As a result of the RSS waveform shown in FIG. 19, the activity of the M100 was early in latency and was large in amplitude in lens color (A). On the other hand, in lens color (F), it was observed that the latency was about 20 ms late, and the amplitude was remarkably lowered. In other words, it is possible to evaluate that lens color A is desirable for the distinction between grass green and yellow (it becomes easy to make a distinction therebetween if contrast is high). In other words, it is understood that when Subject 14 wears lens color A, the subject feels high in the contrast of the grass grain. Additionally, although the point at which the amplitude is observed to be lowered and at which the latency is observed to be delayed was the same as in Subject 14 in lens F according to measurement results in another subject, the latency was the earliest in lens color G in this subject, and it was understood that the most suitable lens color for this subject is lens color G (the graph of the measurement results is not shown).

Although Embodiment 8 showed evaluation examples of the contrast assuming the grass grain, a combination of chromatic colors is not limited to this. For example, on the assumption that the contrast of a scene in which fallen leaves shine in the evening sun is intended to be evaluated, two characteristic colors (e.g., brown RGB (125, 76, 30) and orange RGB (196, 123, 45)) are chosen from a photograph or an image in which the evening sun is reflected in fallen leaves, and a visual stimulus object arranged in brown-orange colors is created, and this visual stimulus object is shown to the subject, and, as a result, it is possible to evaluate the contrast of fallen leaves of a scene in which the fallen leaves shine in the evening sun.

Embodiment 9

Embodiment 9 is an embodiment concerning the design and the evaluation of progressive power lenses. With respect to eyesight, although human visual information is largely affected by central vision to which attention is paid, information by peripheral vision that is dimly input from the periphery at that time is also important. For example, when the front is seen straightly, not only the center but also the periphery is seen (however, a discrimination capability with respect to characters or the like is greatly lowered).

Figure 20:
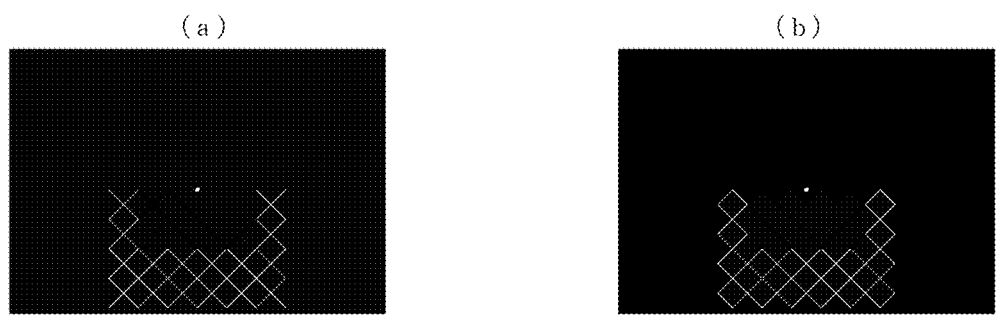
FIG. 20 A visual stimulus object used in Embodiment 9. Examples of visual stimulus objects (a) and (b) that are equal in the total amount of line segments.

In Embodiment 9, visual stimulus objects shown in FIG. 20(a) and FIG. 20(b), respectively, were alternately presented at a visual distance of 1 m for each period of a stimulus of 250 ms with stimulus-to-stimulus intervals of 600 ms, and a subject is allowed to gaze at a fixation point displayed at the center of each visual stimulus object. The two stimulus objects of FIG. 20(a) and FIG. 20(b) have line segments all of which are the same in length, and therefore the stimulus object has an unchangeable brightness, and is not continuously presented, and hence has the advantage that an afterimage is not easily generated. The outer periphery of each visual stimulus object of FIGS. 29(a) and 29(b) is 29°(sidewise)×18°(lengthwise) in visual angle, and dose not display the visual angle 18°×9° with the fixation point as the center of an upper side of a rectangular shape.

Figure 21:
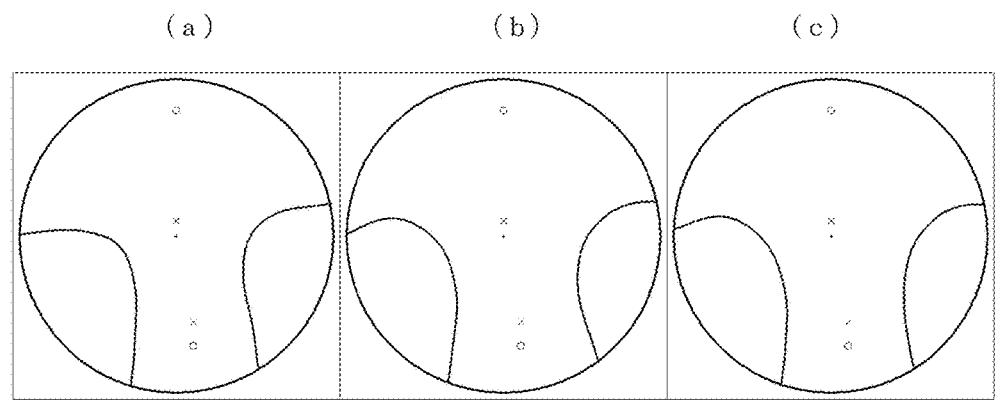
FIG. 21 (a) of FIG. 21 to (c) of FIG. 21 are astigmatism views of the design of three kinds of near-middle progressive lenses that are compared with each other in Embodiment 9. The solid line represents C −1.00.

Subject 15 whose right eye is S −4.00 ADD 2.25 and whose left eye is S −3.50 C −1.00 AX180 ADD 2.25 was allowed to wear Design A, Design B, and Design C each of which has progressive power lenses (near-middle progressive lenses) each having an additional diopter power of 37% on each FP shown in FIG. 21(a) to FIG. 21 (c), and measurement was performed by the 306-channel magnetoencephalograph (arithmetic addition 120 times). In these three kinds of designs, very delicate lens performance is changed according to a trade-off relationship as shown in FIG. 21(a) to FIG. 21(c), and difficulties attend the selection of the best design in computer simulation.

Figure 22:
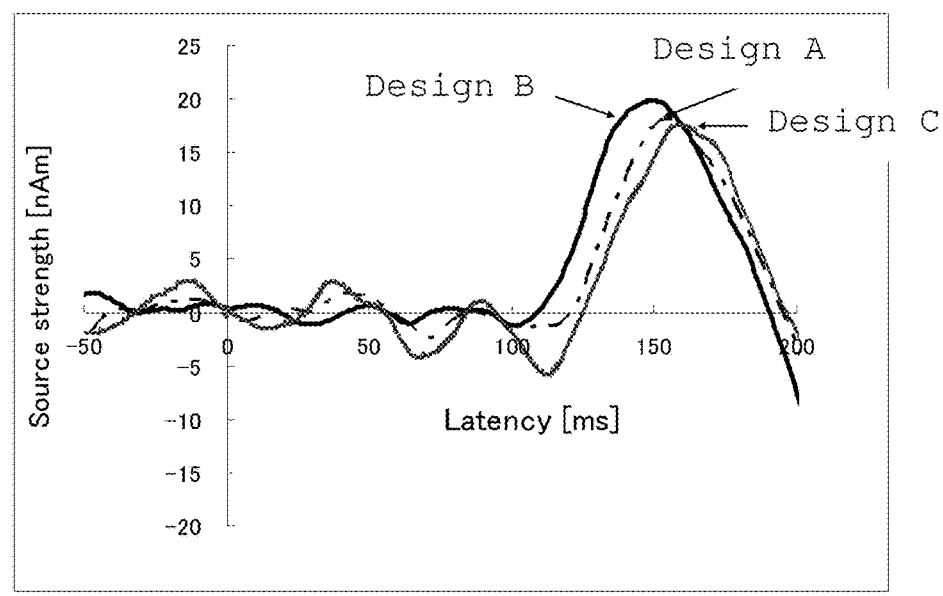
FIG. 22 Activity when designs A to C of the primary visual cortex of Subject 15 that have been separated by a signal source analysis are worn in Embodiment 9.
Figure 23:
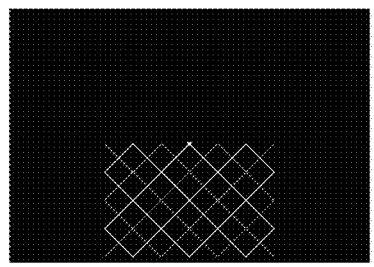
FIG. 23 (a) of FIG. 23 is a visual stimulus object when the vicinity of the fixation point also presents visual information in Embodiment 9, and (b) of FIG. 23 is a visual stimulus object when visual information is not presented to visual angle 9°×4.5° on the assumption that the fixation point is the center of the upper side of a rectangular shape in Embodiment 9
Figure 23:
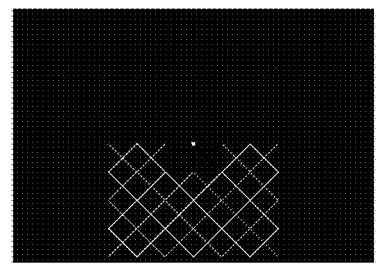

From measurement results obtained by the 306-channel magnetoencephalograph, a multi-signal-source analysis was made by use of BESA (Brain Electric Source Analysis), and the latency of V1 was calculated concerning Designs A to C, and, as a result, it was 155 ms in Design A, it was 149 ms in Design B, and it was 159 ms in Design C as shown in FIG. 22, and it was understood that Design B is the earliest in the latency and shows an excellent result. Thus, it is possible to evaluate the design of the progressive power lens according to the method of Embodiment 9, and to select the most suitable design for the subject, and to perform lens design. When the visual stimulus object was also presented near the center near the fixation point as shown in FIG. 23(a), a difference in the latency between lenses was not observed although each latency of Designs A to C was measured about 20 ms early. Additionally, when an index that does not display the visual angle 9°×4.5° with the fixation point as the center of the upper side of a rectangular shape was presented as shown in FIG. 23 (b), a measurement result closer to the result obtained when that of FIG. 32 was presented was obtained, and it was impossible to measure a difference in lens performance. Therefore, it becomes important not to present about eight degrees with the fixation point as a center.

It is also possible to embody the present invention by making the following modifications.

Although an example was shown in Embodiments 3 to 5 in which the position of Oz in the international 10-20 electrode system is measured, the present invention is not limited to this because the electrode position can also be set according to an activity source to be targeted. For example, when the evoked activity of the tertiary visual cortex is measured, the positions of T5 and T6 of the international 10-20 electrode system are close to an activity source, and therefore it is also possible to set T5 and T6 as electrode positions, respectively. Additionally, although a measurement example of a single electrode in the occipital lobe was shown in Embodiments 3 to 5, it is possible to obtain a more aimed evoked-activity waveform by also measuring electrodes near the frontal lobe or near the head vertex, such as Fz or Cz of the international 10-20 electrode system, and by obtaining a difference waveform with respect to the electrode of the occipital lobe.

Although the chromatically-colored visual stimulus object having two colors was shown as an example in Embodiment 8, it is also possible to allow the visual stimulus object to have more than two colors. For example, if a colorful actual photograph is used as the background and if a combination of line segments having a certain color is presented as a stimulus there, it is possible to evaluate contrast in a state that is even closer to a real scene. Additionally, line segments serving as a stimulus and the background may be arranged by a plurality of colors while imitating coloring in a scene that is aimed for contrast evaluation. In the present embodiment, the two colors were used in order to facilitate explanation.

The use of a chromatically-colored visual stimulus object as in Embodiment 8 makes it possible to simply measure individual characteristics, such as color weakness or color blindness, as the evoked activity of the brain's visual cortex if the evaluation technique of the present invention is employed. In that case, the degree of color weakness is measured as the magnitude or the latency of the evoked activity of the primary visual cortex. Additionally, the measurement of the wearing time of a certain lens makes it possible to evaluate how color weakness or color blindness is improved by that lens. Thus, the chromatically-colored visual stimulus object of the present invention and the evaluation method of spectacle lenses by the evoked activity of, for example, the brain's visual cortex using the visual stimulus object can also be used for inspecting color blindness or color weakness or for evaluating spectacle lenses used to remedy such color blindness or color weakness.

Although a case in which the visual stimulus is presented roughly at 2 Hz (with stimulus-to-stimulus intervals of 500 ms) was described in the embodiment of the evoked activity of the present invention, it is possible to measure the steady state of evoked activity (steady-state visual evoked potential (or steady-state visual evoked field)) by presenting a stimulus at high speed of more than 4 Hz (less than a stimulus-to-stimulus interval of 250 ms) and by performing a frequency analysis by, for example, Fourier transform with respect to a measurement result obtained thereby. Generally, when the magnitude (amplitude) of the evoked activity in the present invention becomes small, the amplitude of steady-state visual evoked potential (or steady-state visual evoked field) shown when a stimulus is presented at 4 Hz or more also becomes small, and therefore, in the present invention, it is also possible to evaluate the steady-state visual evoked potential (or steady-state visual evoked field) while presenting the stimulus at 4 Hz or more and to evaluate spectacle lenses.

Concerning the evaluation of the evoked activity in a specific part of the brain's visual cortex, it is possible to indirectly evaluate the evoked activity in the specific part by evaluating a reaction (activity) correlating with the evoked activity in the specific part. For example, an external stimulus (light) is input to retinal visual cells, is then transmitted to the primary visual cortex, and is transmitted to higher-level brain parts, and thereafter a P300 relating to cognitive judgment is allowed to appear near the head vertex. Therefore, when the reaction time (latency) of the evoked activity of the primary visual cortex is delayed, the succeeding reaction of, for example, the P300 is also delayed, and therefore, for example, the P300 or the like that is a correlating brain reaction may be measured instead of measuring the reaction of the primary visual cortex. A case in which the activity of a specific part, such as the brain's visual cortex, is indirectly evaluated in this way is also included in the present invention.

For example, lenses whose spectral transmittance is changed by an antireflection film or the like formed on the lens surface are also included in lenses whose spectral transmittance is changed by optical absorption or optical reflection, etc., shown in example 21, and it is possible to evaluate the effect and the like of antireflection films of spectacle lenses by employing the present invention.

Besides, it is free to embody the present invention in modes not departing from the gist of the present invention.

The invention claimed is:

1. A method for evaluating spectacle lenses by an evoked activity of a visual cortex of a subject's brain, the method comprising:
   presenting the subject with a visual stimulus object for observation at a peripheral part away from a fixation point to which attention of the subject is paid, wherein the subject is wearing a lens to be evaluated while observing the visual stimulus object, and wherein the visual stimulus object evokes an activity of a specific part of the brain's visual cortex;
   measuring the evoked activity of the specific part of the brain's visual cortex as a change in at least one of an electric potential or a magnetic field of the brain's visual cortex when the visual stimulus object is visually observed by the subject through the lens to be evaluated, wherein the evoked activity is measured using an electroencephalograph, a magnetoencephalograph, or a combination thereof;
   determining an evaluation index for the lens to be evaluated from the measured evoked activity by calculating a magnitude of the change in at least one of the electric potential or magnetic field and a latency in response of the visual cortex to the visual stimulus; and
   evaluating the performance of the lens relative to the subject based on the evaluation index.

2. The method for evaluating spectacle lenses by an evoked activity of a brain's visual cortex according to claim 1,
   wherein measuring the evoked activity includes separating an evoked activity of a primary visual cortex or an evoked activity of a secondary visual cortex from the evoked activity of the brain's visual cortex; and
   wherein evaluating the performance of the lens relative to the subject is based on an evaluation index of the evoked activity of the primary visual cortex separated therefrom or the evoked activity of the secondary visual cortex separated therefrom.

3. The method for evaluating spectacle lenses by an evoked activity of a brain's visual cortex according to claim 1, wherein the visual stimulus object is disposed in a visual lower half area.

4. The method for evaluating spectacle lenses by an evoked activity of a brain's visual cortex according to claim 2, wherein the visual stimulus object is disposed in a visual lower half area.

5. The method for evaluating spectacle lenses by an evoked activity of a brain's visual cortex according to claim 1, wherein measuring the evoked activity includes measuring an evoked potential of an N130 component that is opposite in peak extreme value to a P100 component immediately after the P100 component is evoked by visually stimulating a primary visual cortex of the subject.

6. The method for evaluating spectacle lenses by an evoked activity of a brain's visual cortex according to any one of claim 2 to claim 5, wherein the visual stimulus object consists of a combination of line segments.

7. The method for evaluating spectacle lenses by an evoked activity of a brain's visual cortex according to claim 6, wherein the visual stimulus object consists of at least two kinds of visual stimulus objects that are equal to each other in total length of the line segments of which each visual stimulus object is formed, and the at least two kinds of visual stimulus objects are alternately presented to the subject.

8. The method for evaluating spectacle lenses by an evoked activity of a brain's visual cortex according to any one of claim 2 to claim 5, wherein the visual stimulus object is not presented within a visual angle of 8 degrees from the fixation point to which attention of the subject is paid, excluding the fixation point.

9. The method for evaluating spectacle lenses by an evoked activity of a brain's visual cortex according to any one of claim 2 to claim 5, wherein the visual stimulus is a contrast, and the evoked activity of the brain's visual cortex evoked by this contrast is evaluated.

10. The method for evaluating spectacle lenses by an evoked activity of a brain's visual cortex according to claim 9, wherein the visual stimulus object consists of a combination of chromatic colors.

11. The method for evaluating spectacle lenses by an evoked activity of a brain's visual cortex according to claim 1, wherein the evoked activity is measured using a magnetoencephalography, and the evaluation index is based on a value of a visual evoked magnetic field.

12. The method for evaluating spectacle lenses by an evoked activity of a brain's visual cortex according to claim 1, wherein the evoked activity is measured using an electroencephalograph, and the evaluation index is based on a value of a visual evoked electric potential.

13. The method for evaluating spectacle lenses by an evoked activity of a brain's visual cortex according to claim 1, wherein the spectacle lens to be evaluated is an aspherical lens in which a shape of a peripheral lens part is changed little by little.

14. The method for evaluating spectacle lenses by an evoked activity of a brain's visual cortex according to claim 1, wherein the spectacle lens to be evaluated is a progressive power lens in which a lens shape is changed little by little.

15. The method for evaluating spectacle lenses by an evoked activity of a brain's visual cortex according to claim 1, wherein the spectacle lens to be evaluated is a lens whose spectral transmittance is changed by optical absorption or optical reflection.

16. The method for evaluating spectacle lenses by an evoked activity of a brain's visual cortex according to any one of claim 1 to claim 5, further comprising designing spectacle lenses using the evaluation index.

17. The method for evaluating spectacle lenses by an evoked activity of a brain's visual cortex according to claim 16, wherein the lens used to determine the evaluation index for designing the spectacle lenses is an aspherical lens, a progressive power lens, or a lens whose spectral transmittance is changed by optical absorption or optical reflection.

18. A method for evaluating a plurality of spectacle lenses by an evoked activity of a visual cortex of a subject's brain, the method comprising:
for each lens of the plurality of lenses to be evaluated, presenting the subject with a visual stimulus object for observation at a peripheral part away from a fixation point to which attention of the subject is paid while the subject is wearing the lens, wherein the visual stimulus object evokes an activity of a specific part of the brain's visual cortex;
measuring, for each lens to be evaluated, the evoked activity of the specific part of the brain's visual cortex as a change in at least one of an electric potential or a magnetic field of the brain's visual cortex when the visual stimulus object is visually observed by the subject through the lens, wherein the evoked activity is measured using an electroencephalograph, a magnetoencephalograph, or a combination thereof;
determining, for each lens to be evaluated, an evaluation index based on the measured evoked activity, wherein the evaluation index includes a magnitude of the change and a latency in response of the visual cortex to the visual stimulus object;
evaluating the performance of each lens relative to the subject based on the corresponding evaluation index; and
selecting the lens corresponding to the evaluation index having the greatest magnitude of change, the shortest latency in response, or both the greatest amplitude or magnitude of change and the shortest latency in response.

19. The method of claim 18, wherein the evaluation index of the selected lens has the largest magnitude of change in the electric potential or magnetic field of the brain's visual cortex.

20. The method of claim 18, wherein the evaluation index of the selected lens has the shortest latency in response of the brain's visual cortex to the visual stimulus.

* * * * *